United States Patent [19]

Kotzan et al.

[11] Patent Number: 5,538,687
[45] Date of Patent: Jul. 23, 1996

[54] APPARATUS FOR GENERATING OPTICALLY DETECTABLE SIGNALS BY APPLYING ELECTRICAL POTENTIALS TO SAMPLE LIQUIDS

[75] Inventors: Holger Kotzan, Ladenburg; Mihail-Onoriu Lungu, Buedingen, both of Germany

[73] Assignee: Behringer Mannheim GmbH, Mannheim, Germany

[21] Appl. No.: 357,746

[22] Filed: Dec. 16, 1994

[51] Int. Cl.[6] .................................................. G01N 21/66
[52] U.S. Cl. .................. 422/52; 422/82.05; 250/361 C; G01N/21/66
[58] Field of Search .................. 436/172, 149; 422/52, 81, 82.01, 82.05, 82.08; 435/808; 204/412, 416; 250/361 C; 324/71.1

[56] References Cited

U.S. PATENT DOCUMENTS

| | | | |
|---|---|---|---|
| 5,093,268 | 3/1992 | Leventis et al. | 436/172 |
| 5,147,806 | 9/1992 | Kamin et al. | |
| 5,232,574 | 8/1993 | Saika et al. | 204/418 |
| 5,466,416 | 11/1995 | Ghaed et al. | 422/52 |

FOREIGN PATENT DOCUMENTS

| | | |
|---|---|---|
| 0525212A1 | 2/1993 | European Pat. Off. |
| WO89/10551 | 11/1989 | WIPO |
| 9214138 | 8/1992 | WIPO |

OTHER PUBLICATIONS

Pollard et al. AN 1983:478973 HCA Plus (Abstract Only).
J. Electrochem. Soc.: Electrochemical Science and Technology, vol. 130, No. 7, "Analysis of the Flow–Through Porous Trielectrode Reactor", R. Pollard, Jul. 1983, pp. 1531–1535.

*Primary Examiner*—Jeffrey R. Snay
*Attorney, Agent, or Firm*—Nikaido, Marmelstein, Murray & Oram

[57] ABSTRACT

The invention addresses a measuring cell and a process for carrying out electrochemiluminescence measurements (ECL). The measuring cell has a sample space in which there are disposed a working and a counter electrode. The counter electrode is disposed such that it is located in the light path between the working electrode and the optical detector.

11 Claims, 7 Drawing Sheets

LEGEND

ANTIBODY     MICROPARTICLE

ANALYTE      ECL LABEL

APPARATUS FOR GENERATING OPTICALLY DETECTABLE SIGNALS BY APPLYING ELECTRICAL POTENTIALS TO SAMPLE LIQUIDS

The present invention addresses the field of electrochemiluminescence (ECL) and concerns in particular an apparatus and a process to carry out electrochemiluminescent measurements.

The invention describes improvements of measuring cells having an electrode arrangement in accordance with the invention.

Apparatus and processes for carrying out electrochemiluminescent measurements are known in prior art. Patent application WO 89/10551 describes such an apparatus in detail. The apparatus comprises a measuring cell having an inlet and an outlet and several electrodes disposed in its inside. The two electrodes of a different polarity which are necessary for the ECL measurements are juxtaposed on one level. On the opposite side of this level and within the measuring cell, provision is made for an optical window through which the optical radiation can be detected. Said patent application is predominantly concerned with the electrochemical preparation of the electrodes prior to a measurement in order to provide identical conditions for successive measurements. Reference is herewith made to patent application WO 89/1055 1 in its entirety.

It was an object of the invention to improve existing measuring cells for electrochemiluminescent measurements with respect to sensitivity, reproducibility, and long-term stability.

In accordance with the invention, it has been found that this object can be accomplished by selecting a cell, where the electrodes are arranged such that the working electrode and counter electrode are not disposed on one level so that a partial volume of the measuring cell is enclosed between the two electrodes.

The invention relates to an apparatus for generating optically detectable signals by applying electrical potentials to sample liquids. Said invention comprises a measuring cell for receiving sample liquids, said cell having at least two openings for letting liquids in and out; a voltage source whose voltage is controllable; at least one working electrode which is located inside the measuring cell and which is connected to the first pole of the voltage source; at least one counter electrode which is located inside the measuring cell and which is connected to the second pole of the voltage source; an optical window located in a wall of the measuring cell; the device is characterized in that the at least one counter electrode is located inside the cell between the optical window and the at least one working electrode.

The apparatus of the invention for generating optically detectable signals has a measuring chamber with preferably two openings for the intake and outlet of liquids.

The measuring cell can be manufactured from single piece or several different but connected parts. The materials used in prior art for the measuring cell include plastics, glass, and metals. If the cell is composed of several parts, these parts can be joined to one another by glueing, screwing, riveting, or welding.

The inside of the measuring cell is preferably so configured that it is completely flushed. Preferred embodiments of the inside cell do, hence, not have recesses or the like. It is preferred that the insides have a longitudinal shape which is flattened in a direction perpendicular to the direction of flow.

In the inside of each measuring cell there are at least one working and one counter electrode. The electrodes are preferably attached to the inner walls of the measuring cells. They can be attached, for example, by glueing, melting or pressing.

The at least one working electrode has a planar surface and is electrically connected to a controllable voltage source. Suitable materials for the working electrode are noble metals, such as gold, silver, platinum, palladium, ruthenium, osmium, tungsten, or mixtures therefore. Particularly preferred materials for the electrodes are gold and platinum.

The at least one counter electrode can be one single piece or be composed of several parts which are connected to one another in an electrically conductive manner. The counter electrode preferably consists of two or more strips which are disposed opposite the working electrode. Suitable materials for the counter electrodes are those that are also used for the working electrode. In accordance with the invention, the working and the counter electrode are not disposed in one plane but opposite each other so that a part of the inside of the cell is located therebetween. The at least one working electrode and the at least one counter electrode are disposed on two parallel levels with a part of the cell inside being located therebetween.

For both the working electrode and the counter electrode, it has proven to be advantageous if the surfaces reflect radiation, particularly radiation generated in an ECL process. The surfaces of the electrodes range in an order of magnitude of $mm^2$ to $cm^2$. Usually, the working electrode is a square or rectangle where the lengths of the sides are in a ratio of 1 to appr. 3. The counter electrodes usually have a smaller surface and a longitudinal shape with lengths in a ratio of 3 to appr. 30. Both the working and the counter electrode are preferable configured as thin plates with thicknesses ranging between a few tenth of millimeters up to a few millimeters.

The counter electrode may also be configured as a net-like arrangement or a plate with recesses.

The working electrode is connected to the first pole of a controllable voltage source and the counter electrode is connected to the second pole of said voltage source. The voltage source can be configured such that the voltage can be manually regulated. It is, however, preferred that the voltage source be controlled by a microprocessor or another control device. The voltage source must be able to provide voltages up to a few volts. In accordance with the invention the magnitude and the duration of the voltage can be controlled. In many cycles of processes, the working electrode functions as an anode and the counter electrode as a cathode; it is, however, also possible to switch the polarities of the electrodes.

The voltage to be supplied by the source is mainly, but not exclusively, determined by the redox systems used in the process, particularly by the oxidation potential of the ECL label. Experience has shown that the electrode arrangement of the invention requires lower voltages to generate electrochemiluminescence than do other currently known measuring cells when the same sample liquids and redox systems are used. Such a redox system is shown in U.S. Pat. No. 5,147,806, the content of which is hereby incorporated by reference. Some of the advantages listed above are a result of this working voltage which is lower than the working voltages which were necessary with cells of the prior art. Experience has shown that when the measuring cell in accordance with the invention is used, the luminescence signal is generated much faster by applying the working voltage than it is the case with other known measuring cells. Moreover, the measuring signal of the measuring cell of the invention can be evaluated more exactly since the maximum of the peak is more pronounced.

A window through which electromagnetic radiation from at least one of the ranges infrared, visible, ultraviolet can be passed through is provided in at least one wall of the measuring cell. The entire cell is preferably made of a material which is permeable for at least one of the aforementioned types of radiation. A particularly suitable material for the optical window and/or the entire cell is polymethylmethacrylate.

In accordance with the invention it has also proven to be advantageous that the at least one counter electrode be located at the inner side of the optical window.

The optical window is arranged such that radiation which is generated at the working electrode can at least partly emerge from the measuring cell through the window. Radiation which emerges through the optical window can be detected by means of a detector. Suitable detectors include, for example, photomultipliers and semi-conductor detectors. In the apparatus of the invention, at least part of the at least one counter electrode is disposed in the path of the beams which are generated in the vicinity of the working electrode and emerge from the measuring cell through the optical window. Since at least part of the counter electrode is located in the path of beams emitted by the ECL label, the first assumption was that the beams are shielded which would result in a signal reduction. When compared to measuring cells where the counter electrode is not placed in the path of the beams, it was unexpectedly found that the electrode arrangement in accordance with the invention produces considerably higher signals.

In a preferred embodiment, a magnet can be attached from the outside of the measuring cell to the wall at which the working electrode is disposed in the inside of the measuring cell. Possible magnets are electrical and permanent magnets.

Permanent magnets are preferred as they do not generate heat during operation. In an automated apparatus, the magnet can be moved towards or away from the working electrode by means of a spindle drive or a lever arm.

It is preferred that the inside of the measuring cell be electrochemically connected to a reference cell. The electrochemical coupling can be accomplished, for example, via a liquid-filled capillary gap or a frit. It is essential for an electrochemical coupling that an exchange between charged particles between the inside of the cell and a reference electrode be possible while said exchange be kept to a lowest possible quantity so as to avoid contamination of the liquid in the inside of the cell. Possible reference electrodes are those known in prior art such as an Ag/AgCl electrode or a calomel electrode.

Figure 1:
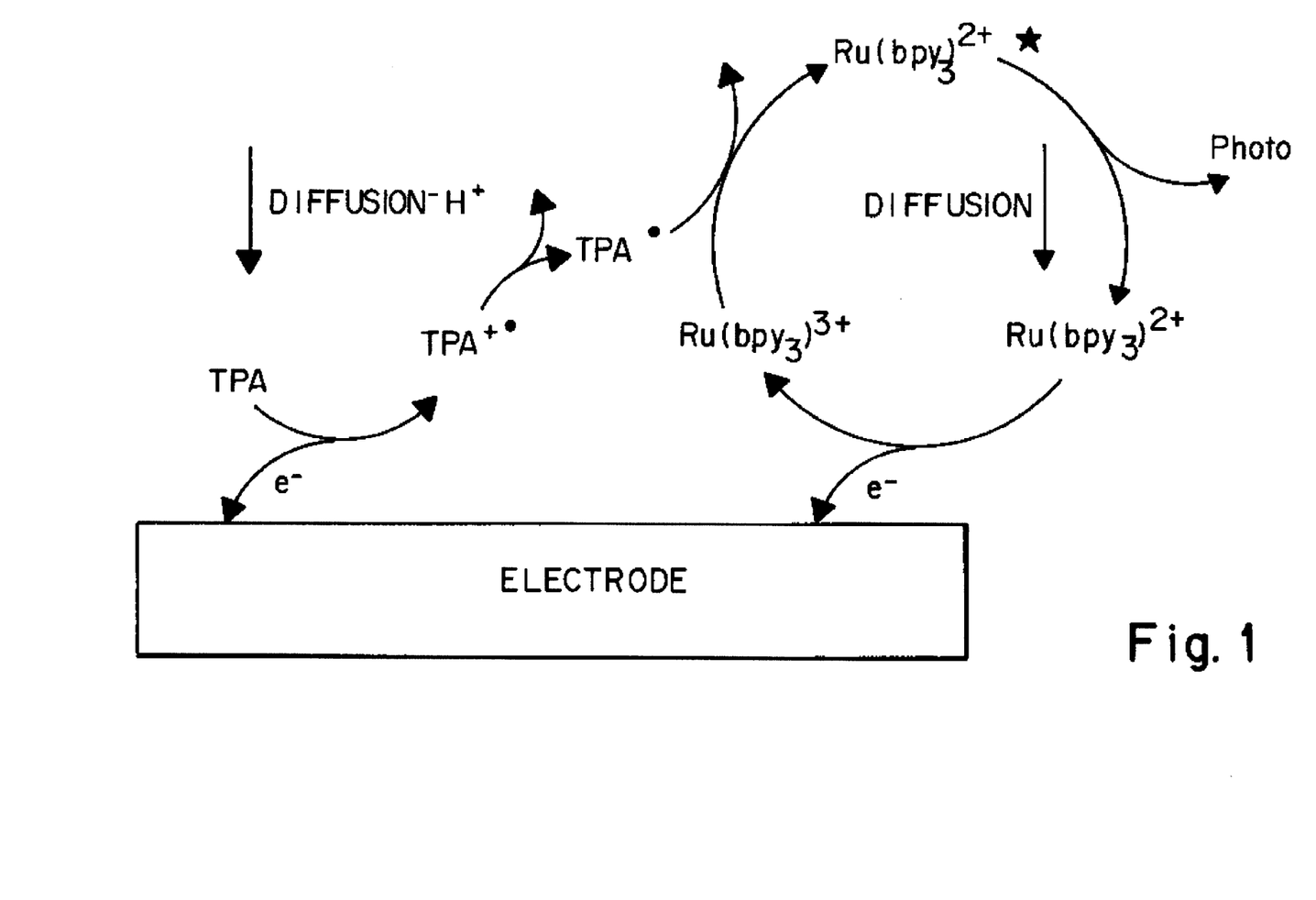
FIG. 1: Diagrammatic representation of the electrode reactions

An apparatus in accordance with the invention was designed to measure electrochemiluminescent phenomena. During an ECL process, chemical species are generated on the surface of an electrode; said species emit electromagnetic radiation in the infrared, the visible, and the ultraviolet range. The electrochemical reactions which occur in such a process are generally described in the aforementioned patent application WO 89/10551. FIG. 1 is an example showing possible electrode reactions. Tripopylamine (TPA) is oxidized at the electrode and then cleaves off a proton. In a second cycle, $Ru(bpy)_3^{2+}$ is oxidized to form $Ru(bpy)_3^{3+}$. The TPA radical and the oxidized ruthenium complex then react and form an excited ruthenium complex which decays back into $Ru(bpy)_3^{2+}$ under the emission of a radiation of 600 nm. This and other electrochemiluminescent systems as they are known in prior art can be used to carry out chemical and immunological analyses.

FIG. 2 is a diagrammatic representation of three different analysis methods that can be implemented with the ECL technology. The format of FIG. 2A is based upon the fact that ECL signals generated by ECL labels which are bound to an antibody differ from those that are freely contained in a solution. FIG. 2B shows a format where a microparticle, which is provided with an antigen, competes with the analyte for an antibody to which an ECL label is attached. If there is no separation, the ECL measurement will produce different signal intensities depending on whether the ECL label was bound to a microparticle or to an analyte molecule. The actual reason for this property has not yet been completely clarified, but it is certain that the different diffusion properties of this species play a role in the electrode reaction. If a separation step is included in the format shown in FIG. 2B, the species which are bound to the microparticle can be separated by applying magnetic forces, provided the microparticle exhibits ferromagnetic properties.

Figure 2A:
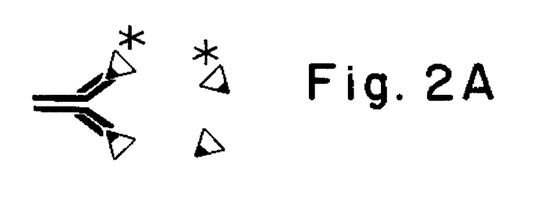
FIG. 2b–2b: Examples for immunological test formats which can be implemented with the measuring cell
Figure 2B:
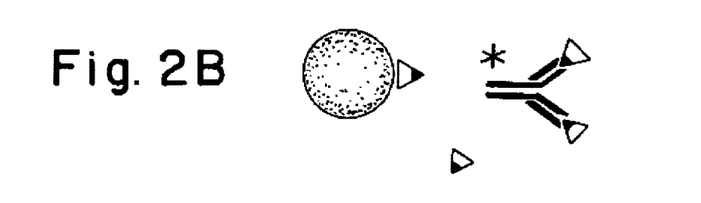
Figure 2C:
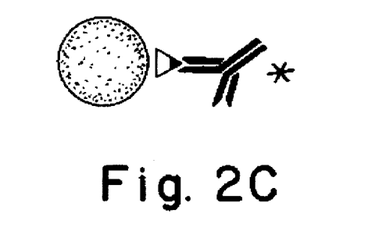
Figure 2D:
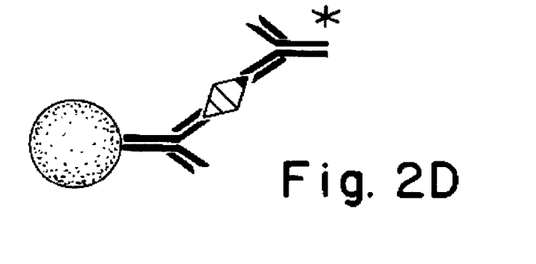

FIG. 2C is a third variant where the signal yield is directly proportional to the concentration of the analyte.

The invention further comprises a process for generating optically detectable signals by applying electrical potential to sample liquids, comprising the following steps.

Filling a measuring cell with sample liquid

Applying a voltage profile to the at least one working electrode and the at least one counter electrode opposite the working electrode in order to generate electrochemiluminescent radiation.

Detecting the emitted radiation which emerges through an optical window

In this process, a measuring cell is first filled with sample liquid. This can be accomplished with an apparatus in accordance with the invention where sample liquid is pumped into the opening of the measuring cell.

Sample liquid is understood to be a mixture of liquids containing analyte solution, reagent solution and, optionally, auxiliary solutions.

Analyte solution, reagent solution, an the optional auxiliary solution can be introduced into the measuring cell either together or successively.

An analyte solution is understood to be a solution, suspension, or emulsion of analyte in a solvent, for example water, acetonitrile, dimethylsulfoxide, dimethylformamide, N-methylpyrolidine, tertiary butyl alcohol or mixtures thereof.

Analyte liquids include whole blood, serum, tissue fluid, saliva, urine, and the like. The analytes to be detected in these analyte liquids include cells, subcellular particles, viruses, nucleic acids, proteins, peptides, hormones, pharmaceutical agents, organic molecules, and the like.

A reagent solution contains an ECL label, i.e. usually an organometallic compound, which emits electromagnetic radiation as a result of chemical and electrochemical reactions. The metal of the organometallic compound is preferably selected from the following group: ruthenium, osmium, rhenium, iridium, rhodium, platinum, palladium, molybdenum, and tungsten. The ECL label can be bound to an entire cell, subcellular particles, viruses, fats, fatty acids, nucleic acids, polysaccharides, proteins, lipoproteins, lipopolysaccharides, glycoproteins, peptides, cellular metabolites, hormones, pharmaceutical agents and their metabolites, alkaloids, steroids, vitamins, amino acids, sugar, organic molecules, organometallic molecules, inorganic molecules, biotin, avidin, or streptavidin.

The above mentioned auxiliary solutions include, for example, rinsing solutions which are suitable to clean the inside of the measuring cell. Accordingly, rinsing solutions may contain detergents, substances which decrease the surface tension, then solvent for organic materials and the like.

In accordance with the invention, it is preferred that the cell be rinsed prior to the actual filling with sample liquid using a cleaning solution or a preparatory solution. A cleaning solution is understood to be any liquid which can be used to remove contamination and residues from the cell, such as detergent solution, solvents and the like. Preparatory solutions are predominately used to make the electrode assume a defined oxidation or surface condition. Preparatory solutions can, hence, contain oxidizing agents, reducing agents or surface-active substances.

Once the cell is filled with sample liquid, a voltage profile is applied to the at least one working electrode and the least one counter electrode.

The voltage profile is a time sequence of voltages of different magnitudes, which is applied between the at least one working electrode and the at least one counter electrode. In the most simple case, a constant, low voltage is applied to the electrodes and suddenly increase to generate the electrode reaction necessary for the ECL reaction. Favorable voltage profiles are described, for example, in patent application WO 90/115 11. The term "voltage profile" identifies a sequence of voltages including all voltage sequences which are necessary for a complete measuring cycle.

According to the invention, it is preferred that the measuring cell and/or the electrodes be cleaned and prepared before the actual measuring step is carded out. The effect of the cleaning and/or preparative solutions in these steps is further supported by applying suitable voltage profiles to the electrodes.

The so far described procedure applies to a homogenous assay, i.e. an analysis where there is no separation of the complex consisting of analyte and ECL label. In accordance with the invention, it is preferred that the complexes consisting of ECL label and analyte be separated prior to activating the electrochemical luminescence. This is preferably done by binding the ECL label either directly to a ferromagnetic particle or by forming a sandwich complex with the analyte and an antigen, which in turn is bound to a ferromagnetic microparticle. The complex containing the ferromagnetic microparticle can be precipitated on the working electrode by using a magnet, whereas excess ECL label is washed away.

Shortly after applying a voltage profile which is suitable for generating an ECL signal, electrochemiluminescent radiation is emitted. The emitted radiation can be detected by means of a detector and the analyte concentration can be concluded from the intensity of the radiation.

As compared to prior art, it is an advantage of the apparatus and the process of the invention that a given electrochemiluminescent reaction can be generated with a voltage that is lower than the one used in currently known apparatus. The redox potential for the redox system of FIG. 1 is at approximately 1.1 V. Reliable measurements with the IGEN measuring cell could be carried out at 2.2 V. With the measuring cell of the invention it was possible to reduce the measuring voltage to 1.4 V.

A reduced measuring voltage has the advantage that fewer interfering side reactions occur which in turn improves the signal/noise ratio.

Moreover, it turned out that the measurement obtained with the measuring cell in accordance with the invention is less dependent on the distribution of the microparticles on the working electrode than measurements carded out with prior art measuring cells. This property of the measuring cells of the invention increases the reproducibility of the analytical detection.

Another advantage of the measuring cells of invention is their improved dynamics which enable more sensitive and more reliable measurements.

An example of the apparatus of the invention and the process of the invention are shown in the figures.

Figure 3:
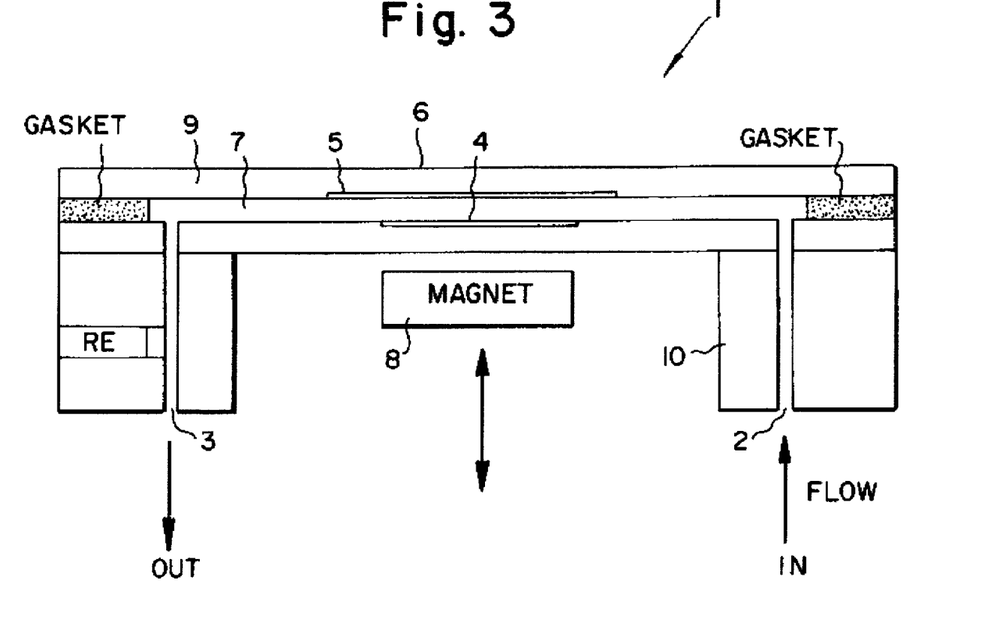
FIG. 3: Lateral view of the measuring cell
Figure 4:
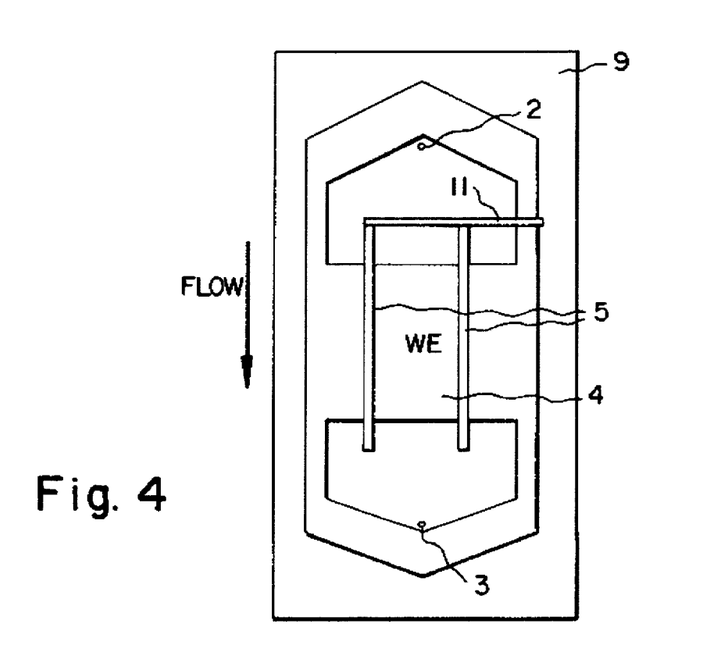
FIG. 4: Top view of the measuring cell

FIG. 3 is a lateral view of the apparatus of the invention. FIG. 4 shows the same apparatus in a top view. The body of the measuring cell (1) comprises several polymethylmethacrylate parts. The inside (7) of the cell has a longitudinal, flat shape. In FIG. 4 it can be seen that the intake and outlet openings (2, 3) are disposed in the obtuse angle of a triangle. With this arrangement it is possible to avoid areas where any residual liquid may remain which is not part of the volume flow while liquid is flowing through the cells. On the bottom (10) of the measuring cell, there is disposed a working electrode (4) of a flat, rectangular shape. The cell shown in this figure has two counter electrodes (5) which have a flat, rod-like shape and are pressed into the upper portion of the measuring cell. A common line (11) connects both counter electrodes (5) to one voltage source. The working electrode as well as the counter electrode shown in this example are both made of platinum. On the side of the measuring cell which is opposite the working electrode, there is an optical window (6). In this example, the cover (9) of the measuring cell is made of polymethylmethacrylate which renders it permeable for visible radiation. Below the working electrode (4), there is a magnet (8) which can be moved either towards or away from it.

Figure 5A:
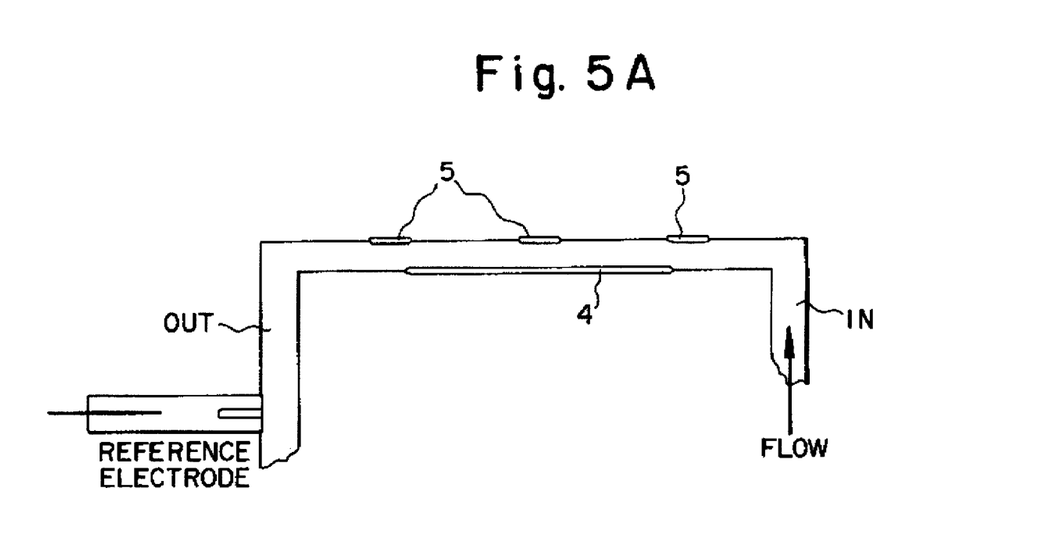
FIG. 5A & 5B: Modified embodiment of a measuring cell in lateral and top view
Figure 5B:
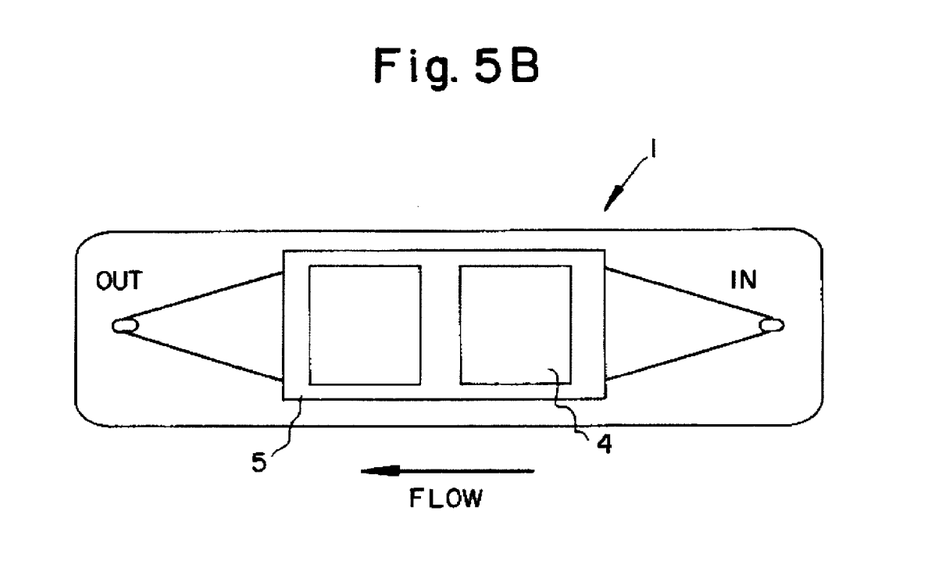

FIG. 5 shows another embodiment of a measuring cell (1) in accordance with the invention. Design and structure of this measuring cell correspond essentially to the one shown in FIGS. 3 and 4. A difference can be found in the configuration of the counter electrode (5). In accordance with the invention, this counter electrode (5) is disposed opposite the working electrode (4), but has the form of a rectangle with two rectangular recesses. The counter electrode (5), hence, has segments which are disposed parallel as well as perpendicular to the direction of flow in the measuring cell.

Figure 6A:
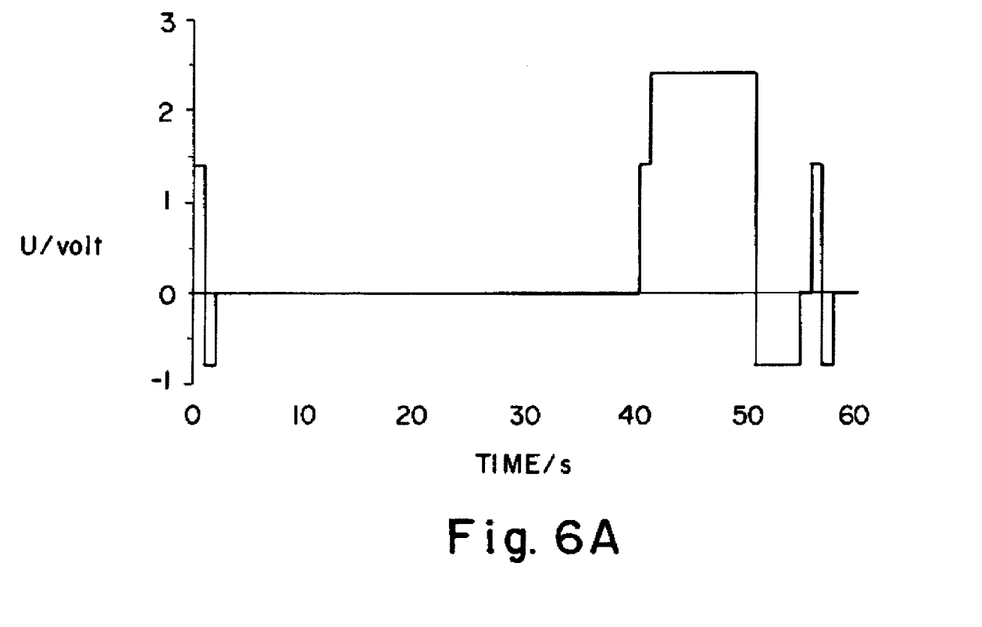
FIG. 6A & 6B: Duration of the voltage to operate the measuring cells of the invention

FIG. 6A shows a voltage profile which is suitable to carry out an ECL reaction with the species tripropylamine and $Ru(bpy)_3^{2+}$ in a measuring cell in accordance with the invention. While the measuring cell is filled with buffer solution, the voltage of +1.4 V is applied for a period of one second and then a voltage of −0.8 V is applied for another second. The purpose of this preparatory phase is to provide a defined surface condition at the working electrode. During the following 39 seconds, the measuring cell is filled with a mixture of analyte, reagent, and buffer solution. A potential (e.g. 0 mV) where no ECL reaction occurs, but which maintains the electrode in a reproducible condition, is applied to the electrodes. In order to generate the ECL signal, a potential of +1.4 V is applied for one second. Subsequently, the measuring cell is cleaned by applying a voltage of +2.4 V over a period of 9.5 seconds followed by a voltage of −0.8 V for a period of 4 seconds. This cleaning process terminates the measuring cycle. The described voltage profile can be again applied for subsequent measurements.

Figure 6B:
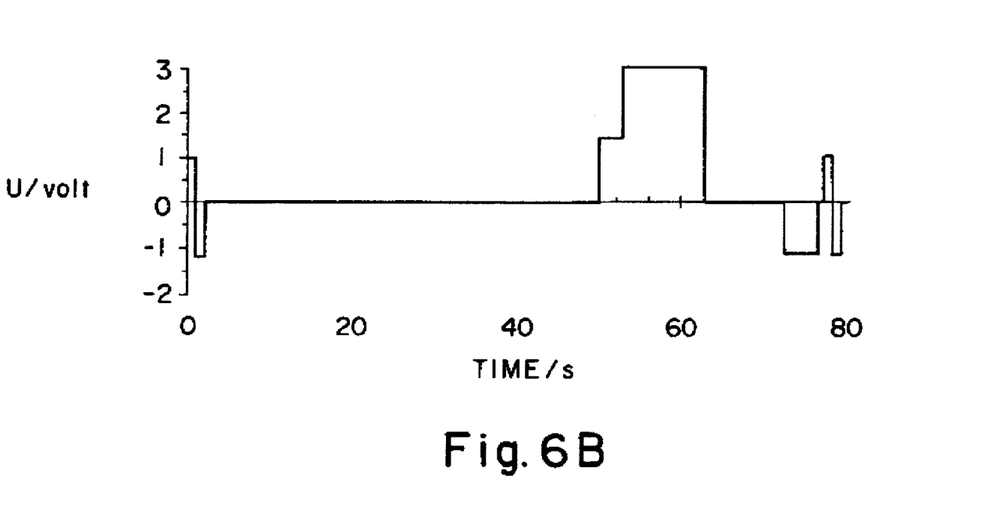

FIG. 6B shows a voltage profile to operate a measuring cell in accordance with the invention using a lower measuring voltage. The following table provides further details on the time intervals at which the voltage was applied and the liquids used in the measuring cell during the individual phases:

| Procedure | Time/s | Voltage/ V | Duration/s | Quantity of liquid/ time | Type of liquid |
|---|---|---|---|---|---|
| Preparation of the measuring cell | 0 | 0 | | 167 µl/s | Buffer solution |
| | 0 | 1 | 1 | | |
| | 1 | 1 | | | |
| | 1 | −1.2 | 1 | | |
| | 2 | −1.2 | | | |
| Filling of the measuring cell | 2 | 0 | 1 | 152 | Sample solution and reagent solution |
| | 11.5 | 0 | 1.2 | 172 | |
| | 12.4 | 0 | 30 | | |
| | 18.4 | 0 | 6 | 33 | Buffer solution |
| | 44.6 | 0 | | 167 | |
| Measurement | 50 | 0 | 1 | none | |
| | 50 | 1.4 | | | |
| Cleaning of the measuring cell | 53 | 1.4 | | 333 | Cleaning solution |
| | 53 | 3 | 9.5 | | |
| | 63 | 3 | | | |
| | 63 | 0 | | | Buffer solution |
| | 72.5 | 0 | 4 | 167 | |
| | 72.5 | −1.2 | | | |
| | 76.5 | −1.2 | 1 | | |
| Preparation of the measuring cell | 76.5 | 0 | 1 | 167 | Buffer solution |
| | 77.2 | 0 | | | |
| | 77.2 | 1 | 1 | | |
| | 78.2 | 1 | | | |
| | 78.2 | −1.2 | | | |
| | 79.2 | −1.2 | | | |
| | 79.2 | 0 | | | |
| | 79.9 | 0 | 0.3 | | |

Figure 7:
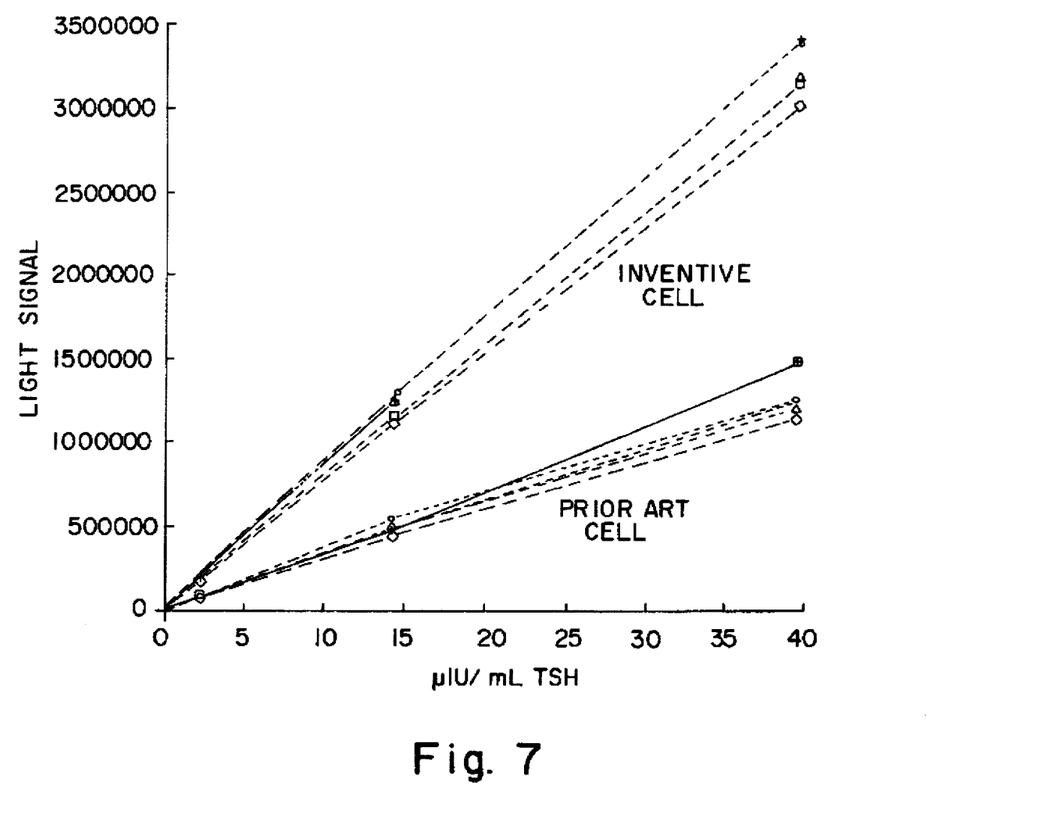
FIGS. 7, 8: Comparison of a measuring cell (K3) in accordance with the invention with a prior art measuring cell (IGEN)
Figure 8:
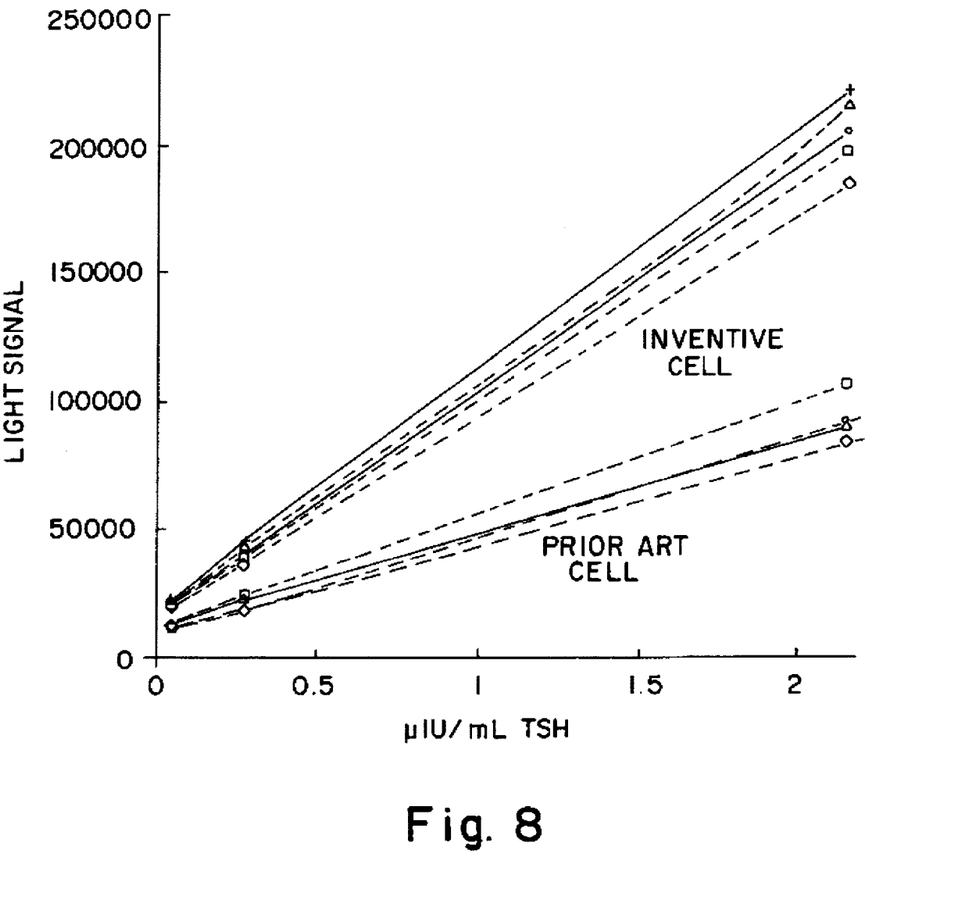

FIGS. 7 and 8 show a comparison of the measuring cell of the invention (designated as concept 3) shown in FIGS. 3 and 4 with the measuring cell by IGEN and described in patent application WO 89/1055 1 for two different concentration ranges of analyte. The light signal plotted on the ordinate in arbitrary units was obtained with a photomultiplier of the Origin 1.0 instrument manufactured by IGEN. The abscissa of the figures shows the TSH (thyroid-stimulating hormone) concentration of the sample.

From the figures it can be understood that the dynamics of the calibration curve is considerably higher when concept 3 cells are used which leads to an increased sensitivity of tests.

The measurements were carried out by incubating 250 µl of a mixture consisting of 50 µl buffer solution IP
50 µl bead suspension
50 µl biotinylated antibody (R1)
50 µl ruthenylated antibody (R2)
50 µl analyte over a period of 16 minutes at room temperature. Then, 150 µl of the incubation mixture were pumped into the measuring cells where the beads were captured on the working electrode with the aid of magnet and then washed.

The composition of the solutions used is as follows:

Buffer Solution IP 50 mM Tris pH 8.0
0.1% CAA
0.01% MIT
0.2% thesit
5% BSA 1
1% bovine IgG

| Biotinylated antibody (R1) | |
|---|---|
| 3.0 µg/ml | MAB <TSH> M1.20-IgG-biotin (Boehringer Mannheim Cat. No. 1352547) |
| 500 µg/ml | MAB <--> IgG (Boehringer Mannheim Cat. No. 1522558) |

| Ruthenylated antibody (R2) | |
|---|---|
| 1.2 µg/ml | MAB <TSH> MA8-F(ab')$_2$-BPRu |

Bead Suspension

600 µg/ml of M280 beads manufactured by Dynal International (Oslo, Norway) were suspended in the buffer.

List of Reference Numerals (1) Measuring cell
(2) Intake opening
(3) Outlet opening
(4) Working electrode
(5) Counter electrode
(6) Optical window
(7) Inside of the measuring cell
(8) Magnet
(9) Cover of the measuring cell
(10) Bottom of the measuring cell
(11) Line

We claim:

1. An apparatus for generating optically detectable signals by applying electrical potentials to sample liquids, said apparatus comprising
   a) a measuring cell for receiving sample liquids, said measuring cell having at least one intake opening and at least one outlet opening for intake and outlet of the sample liquids;
   b) at least one working electrode fixed inside the cell;
   c) at least one counter electrode fixed inside the cell;
   d) a controllable voltage source for providing a controllable voltage to said electrodes, wherein a first pole of said voltage source is connected to said at least one working electrode and a second pole of said voltage source is connected to said at least one counter electrode; said apparatus further comprising
   e) an optical window fixed in a wall of the measuring cell, wherein the at least one counter electrode is fixed at a location inside the cell which is between the optical window and the at least one working electrode.

2. An apparatus according to claim 1, where the at least one working electrode includes a surface which is disposed parallel to the optical window.

3. An apparatus according to claim 1, wherein the at least one working electrode comprises at least one of gold and platinum.

4. An apparatus according to claim 1, wherein the at least one working electrode is configured to reflect optical radiation.

5. An apparatus according to claim 1, further comprising a reference cell which is electrochemically coupled to the inside of the measuring cell.

6. An apparatus according to claim 1, wherein said working electrode is disposed on an inner surface of a first side of said measuring, cell, and said counter electrode is disposed on an inner surface of a second side of said measuring cell, and wherein said first side and said second side of said measuring cell are opposed to each other.

7. An apparatus according to claim 1, comprising at least two counter electrodes, each counter electrode having a flat, rod-like shape.

8. An apparatus according to claim 1, wherein a direction of flow of the sample liquid through the cell is parallel to a longitudinal axis of the at least one counter electrode.

9. An apparatus according to claim 1, wherein said working electrode comprises a planar surface electrode disposed on an inner surface of a first side of said measuring cell.

10. An apparatus according to claim 9, further comprising a magnet disposed adjacent an outer surface of said first side of said measuring cell.

11. An apparatus according to claim 10, further comprising moving means for moving said magnet toward and away from the outer surface of the first side of the cell.

* * * * *

UNITED STATES PATENT AND TRADEMARK OFFICE
CERTIFICATE OF CORRECTION

PATENT NO. : 5,538,687

DATED : July 23, 1996

INVENTOR(S) : Kotzan et al.

It is certified that error appears in the above-indentified patent and that said Letters Patent is hereby corrected as shown below:

Title page, Item [73], line 1, delete "Behringer Mannheim GmbH"

insert therefor -- Boehringer Mannheim GmbH --.

Signed and Sealed this

Twenty-first Day of January, 1997

Attest:

BRUCE LEHMAN

*Attesting Officer*    *Commissioner of Patents and Trademarks*